United States Patent [19]

Gentelia et al.

[11] Patent Number: 5,267,994

[45] Date of Patent: Dec. 7, 1993

[54] ELECTROSURGICAL PROBE

[75] Inventors: John S. Gentelia, Madison; Frank Williams; William Wheatley, both of Utica, all of N.Y.

[73] Assignee: Conmed Corporation, Utica, N.Y.

[21] Appl. No.: 833,001

[22] Filed: Feb. 10, 1992

[51] Int. Cl.$^5$ ..................... A61B 17/32; A61B 17/39
[52] U.S. Cl. ........................ 606/15; 606/41; 606/45; 606/46; 604/35
[58] Field of Search ............... 606/15, 41, 45, 46, 606/47, 48, 49, 50; 604/35

[56] References Cited

U.S. PATENT DOCUMENTS

| | | |
|---|---|---|
| 3,807,404 | 6/1974 | Weissman et al. |
| 4,481,948 | 1/1984 | Sole . |
| 4,593,691 | 12/1986 | Lindstrom et al. |
| 4,660,571 | 4/1987 | Hess et al. ............... 606/41 X |
| 4,724,836 | 2/1988 | Okada ........................ 606/46 |
| 4,815,461 | 3/1989 | Rodriquez . |
| 4,881,524 | 7/1989 | Boebel et al. |
| 4,892,105 | 7/1990 | Prass . |
| 4,936,842 | 6/1990 | D'Amelio et al. ............ 606/50 |
| 4,943,290 | 12/1990 | Rexroth et al. |
| 4,944,738 | 9/1990 | Rodriquez . |
| 5,011,483 | 4/1991 | Sleiste ..................... 606/41 X |
| 5,071,519 | 1/1991 | Rydell et al. |
| 5,100,402 | 2/1992 | Fan . |

FOREIGN PATENT DOCUMENTS 8403829 10/1984 World Int. Prop. O. ............ 606/49

Primary Examiner—Lee S. Cohen
Attorney, Agent, or Firm—Larson & Taylor

[57] ABSTRACT

An electrosurgical probe is provided which reduces the likelihood of arcing from the probe. In addition, the probe provides the ability to place a fiber-optic cable through the probe for providing for laser surgery or for laproscopic examination of the patient. The electrosurgical probe comprises an electrosurgical tip, a cylindrical body attached to the tip, and a base attached to the cylindrical body. The tip may have many different shapes but a spatula shape is generally preferred. The tip has at least one notch in the periphery of the spatula shape for retaining a fiber-optic cable. The cylindrical body is substantially hollow so that suction, irrigation, and laparoscopy may be carried out through the probe. To aid the surgeon in determining dimensions of organs within a patient, the cylindrical body has a plurality of striped regions having a predetermined thickness spaced apart at predetermined intervals on an outer surface of the cylindrical body. The cylindrical body is composed of an insulative material for preventing accidental shock to a patient. To prevent accidental arcing, an insulative layer which substantially covers the electrosurgical tip with at most a 4 mm extension of the electrosurgical tip exposed with no insulative layer.

9 Claims, 2 Drawing Sheets

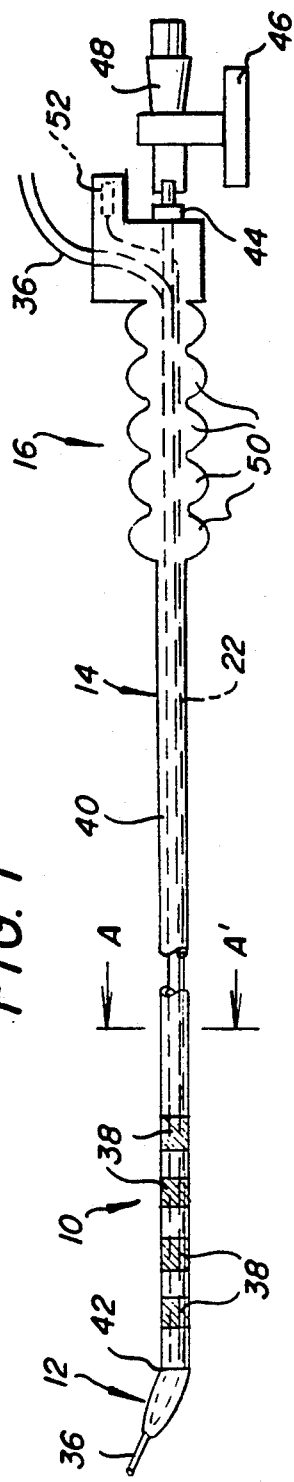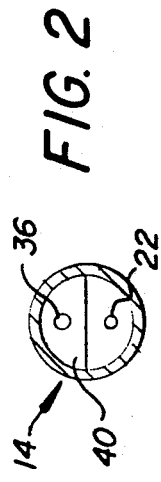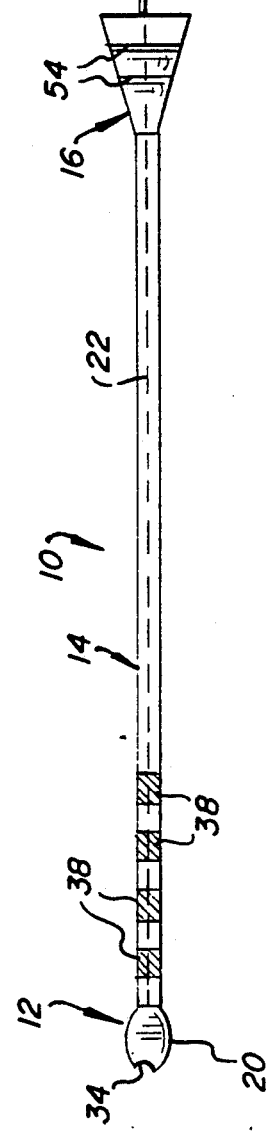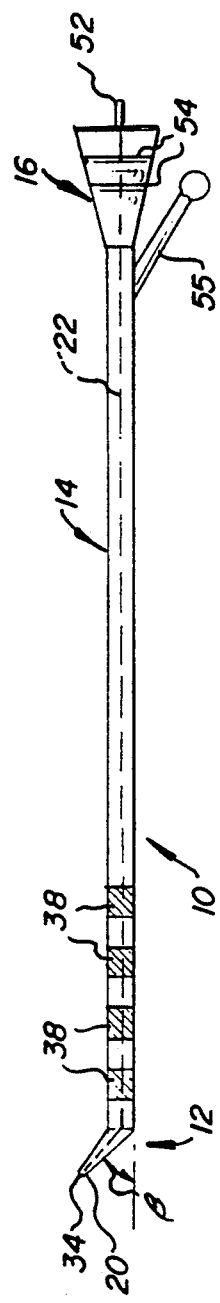

ELECTROSURGICAL PROBE

FIELD OF THE INVENTION

This invention relates generally to electrosurgical probes and more specifically, to a multiutility probe with an improved tip structure for use in electrosurgery.

BACKGROUND OF THE INVENTION

Laproscopic surgery has become a popular technique among many surgeons. Laparoscopy allows a surgeon to limit the intrusiveness of conventional operating techniques and thus reduce the amount of scar tissue and decrease the amount of healing time associated with surgery.

Laparoscopy is the visual examination of the interior of the abdomen of a patient by the use of a laparoscope, a long slender instrument. Through appropriate optical techniques, the surgeon is able to view the interior of the patient's abdomen.

The procedure is started by the insertion of several trocars. A trocar is a device that is used to puncture the abdomen wall and is inserted through a hollow sleeve, called a cannula which is then positioned in the opening created by the trocar. In this surgical procedure, the laparoscope is inserted into one of the cannulas and other cannulas are used to pass surgical instruments into the abdomen which instruments are utilized to carry out surgical procedures on the internal organs of the patient.

Once an abnormality is found, the surgeon may remove the abnormality by either electrosurgery or by laser techniques. The determination of which technique to use depends on the personal preference of the surgeon. Obviously, there are a significant number of tools involved in laparoscopic surgery. The time and effort involved in switching tools to change from electrosurgery to laser surgery can be considerable. By switching tools in the middle of an operation, there is an increased chance that the abdomen may deflate and thus cause damage to the patient and further delay. There have been many attempts to create multi-purpose tools that reduce the risk to the patient while also increasing the utility of the device to the surgeon.

Several U.S. patents disclose devices that are designed to attempt to increase the effectiveness of electrosurgical probes while providing for the safety of the patient. U.S. Pat. No. 4,481,948 (Sole) discloses an electrosurgical probe that has a wire loop which is used to cauterize a section of the patient's body. This probe has a substantial portion of the electrosurgical tip exposed to the patient. This exposure of the tip may cause unintentional arcing from the tip to surrounding tissue and organs. This arcing will cause damage to surrounding tissue/organ and thus increase the recovery time and potentially damage the tissue/organ.

U.S. Pat. No. 4,593,691 (Lindstrom et al.) discloses interchangeable electrosurgical probes and a power supply unit. Each probe disclosed has a tip region with a substantial portion thereof exposed to surrounding tissue. This presents the potential for accidental arcing which may cause damage to surrounding tissue.

Other examples of electrosurgical probes that do not provide insulation over a substantial portion of the operating tip include: U.S. Pat. No. 4,943,290 (Rexroth et al.); U.S. Pat. No. 4,892,105 (Prass); and U.S. Pat. No. 3,807,404 (Weisman et al.). Generally, existing instruments, shaped as spoons, spatulas, hooks, and hockey sticks, have insulated shafts with non-insulated ends of approximately 5 mm to 20 mm. This non-insulated area increases the potential for arching.

Several U.S. patents disclose the use of hollow insertion devices to place a fiber-optic cable that may be used in either laser surgery or as a laparoscope. U.S. Pat. Nos. 4,815,461 and 4,944,738, both by Rodriguez, disclose a tube having a head section that is adjustable. This adjustable head section allows for a back stop during laser surgery. U.S. Pat. No. 4,881,524 (Boebel et al.) discloses a device for guiding a fiber-optic cable for viewing the interior of a patient. None of the above cited references provide a multi-purpose probe that allows electrosurgery to occur from a substantially insulated tip and also allow a fiber-optic cable to be inserted into a patient for allowing laser surgery or for viewing the interior of the patient.

Although all of the above-discussed devices relate to electrosurgical probes, they have the various disadvantages mentioned above.

SUMMARY OF THE INVENTION

According to the invention, an electrosurgical probe is provided which reduces the likelihood of arcing from the probe. In addition, the probe provides the ability to place a fiber-optic cable through the probe for providing for laser surgery or for laproscopic examination of the patient. The electrosurgical probe comprises an electrosurgical tip, a cylindrical body attached to the tip, and a base attached to the cylindrical body. The tip may have many different shapes but a spatula shape is generally preferred. The tip has at least one notch in the periphery of the spatula shape for use with a fiber-optic cable. The cylindrical body is substantially hollow so that suction, irrigation, and laparoscopy or laser surgery may be carried out through the probe. To aid the surgeon in determining dimensions inside of a patient, the cylindrical body has a plurality of striped regions having a predetermined thickness which regions are spaced apart at predetermined intervals on the outer surface of the cylindrical body. The cylindrical body is composed of an insulative material for preventing accidental shock to a patient. A means for providing electrical current to the electrosurgical tip from the distal end of the probe is also provided. To prevent accidental arcing, an insulative layer which substantially covers the electrosurgical tip and allowing at most a 4 mm extension of the electrosurgical tip to be exposed is provided.

The ability to use a fiber-optic cable in combination with the probe allows a surgeon to perform an operation without switching tools in the middle of the operation. It also avoids the need to make additional punctures in the patient's chest for the positioning of additional equipment.

Other features and advantages of the invention will be set forth in the following detailed description of the preferred embodiment of the invention.

BRIEF DESCRIPTION OF THE DRAWINGS

FIG. 1 is a side elevational view of an electrosurgical probe constructed in accordance with a preferred embodiment of the invention;

FIG. 2 is a cross sectional view of the probe of FIG. 1 taken along the line demarked A—A';

FIG. 3 is a side elevational view of an alternate embodiment of the probe of FIG. 1

FIG. 4 is a plan view of the probe of FIG. 3; and

DESCRIPTION OF THE PREFERRED EMBODIMENTS

Referring to FIGS. 1 and 2, an electrosurgical probe constructed in accordance with a preferred embodiment of the invention is shown. The probe 10 is composed of a tip 12, a cylindrical body 14 attached to the tip 12 and a base 16. The electrosurgical tip 12 is composed of a conductive material that preferably has a low reflectivity to light. Tip 12 may take various shapes depending on the particular operation being performed and the preferences of the surgeon. A variety of tip structures are illustrated in FIGS. 5A–5F.

Figure 5A:
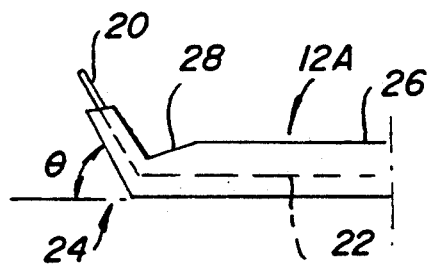
FIGS. 5A–5F are side elevational views of tips for the probe of FIGS. 1 and 3.

FIG. 5A illustrates a modified hockey stick shaped tip 12A. The tip 12A is composed of an electrode 20, a conductive wire 22, and an insulative layer 24 which covers both the conductive wire 22 and a portion of the electrode 20. As may be seen by FIG. 5A, the insulative layer 24 is in the shape of a hockey stick. The insulative layer 24 is generally cylindrical in shape and forms a base 26. Base 26 attaches to the cylindrical body 14. Hockey stick shaped tip 12A may be attached permanently to cylindrical body 14 or may designed to be removable so as to facilitate the changing of the tip. The cylindrical base 26 tapers at point 28 and then bends at a predetermined angle θ with respect to the longitudinal axis of cylindrical base 26. The angle θ may be between 0° and 90°. In a preferred embodiment, angle 0 is approximately 30 . The electrode 20 extends from the insulative body a distance of at most 4 mm. It has been determined through extensive use that an exposed electrode of a length greater than 4 mm substantially increases the likelihood of accidental arcing. An electrode of a length significantly shorter than 4 mm tends to be very difficult for the surgeon to use.

Figure 5B:
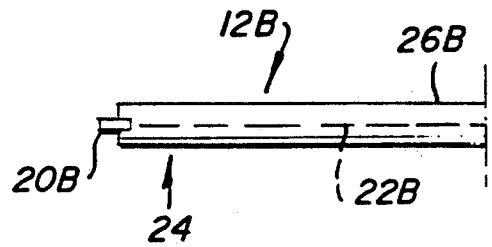

FIG. 5B is an alternate embodiment of the tip 12A of FIG. 5A. In this embodiment, tip 12B is formed by cylindrical base 26B, conductive wire 22B, electrode 20B, and insulative layer 24, similar to that of FIG. 5A. In this embodiment, the electrode 20B extends along the longitudinal axis of the cylindrical base 26.

Figure 5C:
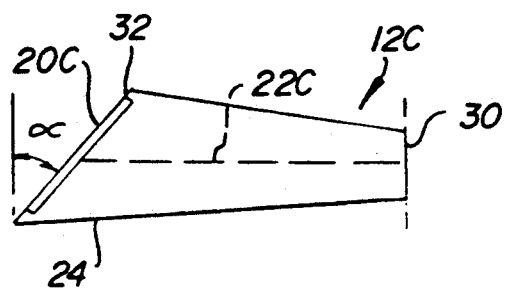

FIG. 5C is another alternate embodiment of the tip 12A of FIG. 5A. Tip 12C comprises a generally conical shaped base 30, a conductive wire 22C extending through the base, and an electrode 20C disposed on the end face 32 of the tip 12A. It can be seen that the end face 32 on which the electrode 20C is mounted is tapered and has the widest diameter at the point that the electrode 20C is attached to wire 22C. As may be seen in FIG. 5C, the face 32 is angled towards the back of the conical base 30. The angle α has a range from 10° to 70°. In a preferred embodiment angle o is approximately 45°. As in FIG. 5A, insulative layer 24 covers the conical base 30, conductive wire 22 and all but 4 mm of electrode 20.

Figure 5D:
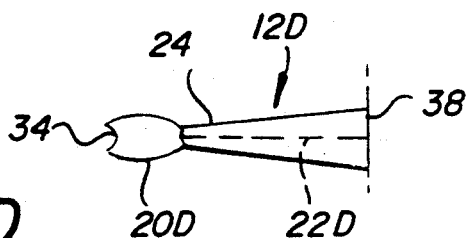
Figure 5E:
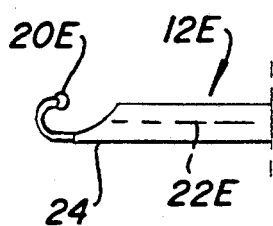
Figure 5F:
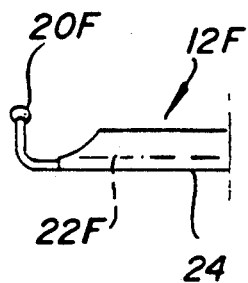

FIG. 5D illustrates the preferred embodiment of tip 12D. In this embodiment, tip 12D has a spoon shaped electrode 20D. On the outer periphery of the electrode 20D, there is at least one notch 34. Notch 34 provides a retainer for a fiber-optic cable 36, illustrated in FIG. 1. The fiber-optic cable 36 may be used as a laparoscope, to get a better view of the operating field, or in laser surgery. The ability to use a fiber-optic cable in combination with the probe allows a surgeon to perform the operation without switching tools in the middle of the operation. It also avoids the need to make additional punctures in the patient's chest for the positioning of needed equipment. In this embodiment, electrode 20D is attached to a conical section 38 that tapers to the electrode 20D. A conductive wire 22D provides connectivity between a power source and the electrode 20. As in the above tips 12A–C, an insulative layer is provided to protect from accidental shock and arcing. Insulative layer covers electrode 20 and allows a maximum of 4 mm of the electrode to be exposed. FIG. 5E illustrates a tip having a J shaped conductive ball as an electrode and FIG. 5F discloses a tip with an L shaped ball as an electrode.

In the above embodiments for the tips, the maximum diameter of the tip will not exceed 10 mm. This is to allow the use of the probe in a 10 mm (id) cannula. Also, it should be noted that insulative layer 24 comprises an integral part of the tip, i.e. by the selection of insulative material for elements 26, 30, and 38 no additional protective layer is required.

Referring to FIGS. 1 and 2, the tip 12 is attached to cylindrical body 14. This attachment may be integral or may be detachable for allowing the changing of tips 12. The cylindrical body 14 is composed of a non-conductive material so that the patient is shielded from the possibility of electrical shock. In a preferred embodiment, the tip 12 is bent at an angle β and this angle is approximately 30°. Located on the outer surface of cylindrical body 14 is a plurality of stripes 38. These stripes are used to aid a surgeon in determining the size of internal parts of the body during the operation. In a preferred embodiment, the stripes are 5 mm wide and are spaced apart by 5 mm. Attached to the distal end of the cylindrical body 14 is a handle 16. In the disclosed embodiment, the handle 16, is provided with a plurality of bulbous protrusions 50 for gripping by the surgeon. Since the shape of the handle is symmetric, a surgeon may rotate the probe at will.

The cylindrical body 14 is substantially hollow to provide a channel 40 (FIG. 2) which extends through the handle 16. This channel 40 may be used for suction, irrigation, or the placement of a fiber-optic cable 36. At one end of channel 40 is a mouth 42 through which channel 40 extends to permit flow of gas or fluid into the body cavity and to receive the end of the fiber optic cable to permit viewing of the body cavity. At the opposite end of channel 40 is a flange 44. Attached to the flange 44, is a T shaped valve 46. Valve 46 may be opened to insert a suction or irrigation tube through port 48. A conductive wire 22 extends from the tip 12 to a connector 52. It should be noted that the connector 52 may be either a male or female connector and may be either covered as in FIG. 1 or exposed as in FIGS. 3 and 4.

Referring now to FIGS. 3 and 4, alternate embodiments of probe 10 are illustrated. In the FIG. 3 embodiment, there is provided a passageway 55 which is connected with a passageway through cylindrical body 14 to irrigate, suction or pass a fiber optic cable therethrough. In the FIG. 4 embodiment, cylindrical body 14 is not provided with a central passageway and thus there is no provisions for suction, irrigation, or a fiber-optic cable. The base 16 is formed by a conical section that tapers outwardly from cylindrical body 14 and provides an enlarged coupling to connect wire 52 to a power source. In a preferred embodiment, the base 16 has raised ribs 54 for aiding in the gripping of the probe.

Although the present invention has been described to specific exemplary embodiments thereof, it will be understood by those skilled in the art that variations and modifications can be effected in these exemplary embodiments without departing from the scope and spirit of the invention.

What is claimed is:

1. An electrosurgical probe comprising, in combination, an elongated cylindrical body, a passageway extending through the cylindrical body, a handle secured to a proximal end of the cylindrical body, a conductive electrosurgical tip secured to a distal end of the cylindrical body, an insulative layer disposed over the surface of a portion of the conductive tip, said insulative layer extending from the distal end of the cylindrical body for a length so that not more than 4 mm of an outer end portion of the conductive tip is exposed, a conductive wire extending from the conductive tip through the cylindrical body to the handle, a fiber optic cable extending through the handle, the cylindrical body and conductive tip with a distal end of fiber optic extending outwardly beyond the conductive tip, and means mounted on the handle for mounting a suction or irrigation system in communication with the passageway extending through the cylindrical body.

2. The probe recited in claim 1 wherein said electrosurgical tip is spatula shaped.

3. The probe recited in claim 2 wherein said spatula shaped tip has at least one notch in the periphery of said spatula shaped tip supporting the fiber-optic cable.

4. The probe recited in claim 2 wherein said spatula shaped tip is angled at least 30° with respect to a centerline of said cylindrical body.

5. The probe recited in claim 1 wherein said electrosurgical tip is spoon shaped.

6. The probe recited in claim 5 wherein said spoon shaped tip has at least one notch in the periphery of said spoon shaped tip supporting the fiber-optic cable.

7. The probe recited in claim 5 wherein said spoon shaped tip is angled at least 30° with respect to a centerline of said cylindrical body.

8. The probe recited in claim 1 wherein said electrosurgical tip is shaped as a hockey stick.

9. The probe recited in claim 1 wherein said electrosurgical tip is hook shaped.

* * * * *